United States Patent [19]

Kaiser

[11] 4,443,611

[45] Apr. 17, 1984

[54] LIQUID PHASE PREPARATION OF 2-H-2-OXAZOLINES AND 2-SUBSTITUTED-2-OXAZOLINES

[75] Inventor: Mark E. Kaiser, Midland, Mich.

[73] Assignee: The Dow Chemical Company, Midland, Mich.

[21] Appl. No.: 415,077

[22] Filed: Sep. 7, 1982

Related U.S. Application Data

[63] Continuation of Ser. No. 966,698, Dec. 5, 1978, abandoned, which is a continuation-in-part of Ser. No. 758,239, Jan. 10, 1977, abandoned, and a continuation-in-part of Ser. No. 875,280, Feb. 6, 1978, abandoned, and a continuation-in-part of Ser. No. 756,155, Jan. 3, 1977, abandoned.

[51] Int. Cl.$^3$ .......................................... C07D 207/20
[52] U.S. Cl. ..................................................... 548/239
[58] Field of Search ......................................... 548/239

[56] References Cited

U.S. PATENT DOCUMENTS 4,035,309  7/1977  Brois ................................... 548/239

FOREIGN PATENT DOCUMENTS 1483682  8/1977  United Kingdom .

*Primary Examiner*—Anton H. Sutto
*Attorney, Agent, or Firm*—Charles J. Enright

[57] ABSTRACT

2-H-2-Oxazolines are prepared by contacting in liquid phase a N-($\beta$-hydroxyalkyl)formamide with a small but catalytic amount of an inorganic zinc salt at elevated temperatures. Similarly, 2-substituted-2-oxazolines are prepared by contacting N-(2-hydroxyalkyl)carboxamides with a small but catalytic amount of an inorganic zinc salt. As an example, 2-H-2-oxazoline was prepared in approximately 72 percent yield by warming a mixture of N-($\beta$-hydroxyethyl)formamide with a catalytic amount of zinc chloride at a temperature of from 180° C. to 185° C./50 mm Hg for 2.2 hours. In this reaction, the desired oxazoline product was recovered as a codistillate with water during the course of the reaction.

8 Claims, No Drawings

LIQUID PHASE PREPARATION OF 2-H-2-OXAZOLINES AND 2-SUBSTITUTED-2-OXAZOLINES

CROSS-REFERENCE TO RELATED APPLICATIONS

This application is a continuation of Ser. No. 966,698, filed Dec. 5, 1978, now abandoned which is a continuation-in-part of abandoned application Ser. No. 758,239, filed Jan. 10, 1977; copending, abandoned application Ser. No. 875,280, filed Feb. 6, 1978; and copending, abandoned application Ser. No. 756,155, filed Jan. 3, 1977.

BACKGROUND OF THE INVENTION

The 2-H-2-oxazolines form a known class of compounds having several members. 2-H-2-Oxazoline is the first member of this series and is the "simplest" molecule. It corresponds to formula I.

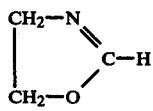

The 2-H-2-oxazolines and particularly I above are generally quite different from the corresponding 2-substituted-2-oxazolines. This is illustrated by the fact that many conventional processes for preparing 2-substituted-2-oxazolines are not particularly satisfactory for the preparation of the corresponding 2-H-2-oxazolines.

For example, many 2-substituted-2-oxazolines are prepared by dehydrochlorinating a β-chloroalkyl carboxamide with aqueous alkali. However, this process reportedly produced I in only very low yields and was accompanied by decomposition of the desired product. (H. Wenker, J. Am. Chem. Soc., 60, 2152 (1938)).

Another common technique for preparing oxazolines is the cyclodehydration of N-(β-hydroxyalkyl)carboxamides over various catalysts. Litt et al. (U.S. Pat. No. 3,681,329) claim that 2-H-2-oxazolines could be prepared by contacting the appropriate carboxamides with compounds of manganese, cobalt, molybdenum, tungsten and the rare earth metals. Unfortunately, there is no experimental data in Litt et al. which would substantiate this allegation. Hess teaches in Canadian Pat. No. 536,594 and British Pat. No. 758,972 that I can be prepared by a cyclodehydration of N-(β-hydroxyethyl)formamide in the presence of a dehydrating agent (specifically, diatomaceous earth, sulfuric acid, aluminum oxide and iron oxide). The yields were higher than the yield reported by Wenker but were still commercially unsatisfactory.

Eisenbraun (U.S. Pat. No. 3,312,714) teaches the preparation of 2-oxazolines from N-(2-hydroxyethyl)amides using a solid inorganic borate or inorganic salt of a boric acid. 2-Oxazoline yields of from about 63 to 77 percent are reported.

More recently, Ito et al. (J. Am. Chem. Soc., 95:13, 4447 (1973)) reported that 2-H-2-oxazolines and oxazines could be prepared by reacting isonitrile with amino alcohols in the presence of a small amount of silver cyanide. Ito et al. report that I was thus produced in 67 percent yield. Isonitrile and silver cyanide appear to be very unique in this particular reaction.

The chemistry of oxazolines has been reviewed by Wiley et al., Chemical Reviews, Vol. 44, 447–476 (1949), Seeliger et al., Angew. Chem. International Edition, Vol. 5, No. 10, 875–888 (1966), and by Frump, Chemical Reviews, 1971, Vol. 71, No. 5, 483–505. Other references have been classified by the U.S. Patent and Trademark Office under the classification of 260/307F.

SUMMARY OF THE INVENTION

It has now been discovered that 2-H-2-oxazolines are prepared by reacting by contacting in liquid phase a N-(β-hydroxyalkyl)formamide with a small but catalytic amount of an inorganic zinc salt. Similarly, 2-substituted-2-oxazolines are prepared by contacting N-(2-hydroxyalkyl)carboxamides with a small but catalytic amount of an inorganic zinc salt. The reaction is normally conducted at an elevated temperature and preferably under reduced pressure.

DETAILED DESCRIPTION OF THE INVENTION

The N-(β-hydroxyalkyl)carboxamides used in the instant process are a known class of compounds which can be represented by the formula

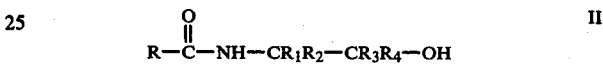

wherein R is hydrogen, a hydrocarbon or an inertly-substituted hydrocarbon group and $R_1$–$R_4$ are hydrogen or inert organic radicals. By "inert" is meant inert in the instant process. When R is hydrogen, the carboxamide reactant is properly called an N-(β-hydroxyalkyl)-formamide.

The formamide compounds are typically prepared by reacting a lower alkyl formate (e.g., methyl formate) or formic acid with an ethanolamine of the formula IV shown below. The carboxamides are typically prepared by reacting a carboxylic acid (RC(O)OH) or a lower alkyl ester of the carboxylic acid with an ethanolamine of the formula

wherein $R_1$–$R_4$ have the aforesaid meaning. The formic acid/amine salt or carboxylic acid/amine salt which is formed initially in these reactions can be used in the instant process in place of the formamide or carboxamide. When such formic acid/amine salts or carboxylic acid/amine salts are used, the formamide or carboxamide is generated in situ. In formulas II and III, $R_2$ and $R_4$ are each preferably hydrogen and $R_1$ and $R_2$ are hydrogen, lower alkyl ($C_1$–$C_6$), hydroxymethyl or alkanoyloxymethyl (alkyl-C(O)—O—$CH_2$—) groups of up to about 17 carbon atoms. More preferably, $R_1$–$R_4$ are each hydrogen. These preferences are based upon the commercial availability of the ethanolamines. N-(β-hydroxyethyl)formamide is the most preferred reactant for use in the instant process which leads to the preparation of 2-H-2-oxazoline. Other suitable N-(β-hydroxyalkyl)formamides include compounds of formula II having the following values for $R_1$–$R_4$:

TABLE I

| $R_1$ | $R_2$ | $R_3$ | $R_4$ |
|---|---|---|---|
| $CH_3$ | H | H | H |
| $CH_3$ | $CH_3$ | H | H |
| $CH_2OH$ | $CH_2OH$ | H | H |
| $C_4H_9$ | H | H | H |

TABLE I-continued

| $R_1$ | $R_2$ | $R_3$ | $R_4$ |
|---|---|---|---|
| $C_6H_5$ | H | $C_6H_5$ | H |
| $CH_3$ | H | $CH_3$ | H |
| $C_6H_4CH_3$ | H | $CH_3$ | H |
| $C_{17}H_{35}C(O)OCH_2$ | H | H | H, |
| and other like compounds. | | | |

R in formula II, when R≠ hydrogen, is preferably alkyl of from 1 to about 17 carbon atoms or phenyl and is more preferably methyl, ethyl or phenyl and is most preferably methyl or ethyl. Examples of suitable N-(β-hydroxyalkyl)carboxamides include compounds of formula II having the following values for R and $R_1$–$R_4$:

TABLE II

| R | $R_1$ | $R_2$ | $R_3$ | $R_4$ |
|---|---|---|---|---|
| $CH_3$ | H | H | H | H |
| $CH_3$ | $C_4H_9$ | H | H | H |
| $CH_3$ | $C_2H_5$ | $C_2H_5$ | H | |
| $C_2H_5$ | H | H | H | H |
| $C_2H_5$ | $CH_2OH$ | $CH_2OH$ | H | H |
| $C_2H_5$ | $CH_2O(O)C-C_{17}H_{35}$ | H | H | H |
| $C_3H_7$ | $C_6H_5$ | H | $C_6H_5$ | H |
| $C_7H_{15}$ | $CH_3$ | H | H | H |
| $C_9H_{19}$ | $CH_3$ | $CH_3$ | H | H |
| $C_{11}H_{23}$ | $CH_3$ | H | $CH_3$ | H |
| $C_{17}H_{35}$ | H | H | H | H |
| $C_6H_5$ | H | H | H | H |
| $C_6H_4CH_3$ | $C_6H_5$ | H | $CH_3$ | H |
| $C_6H_5CH_2$ | H | H | $CH_3$ | $CH_3$ |
| $CH_3(CH_2)_7CH=CH(CH_2)_7$ | H | H | H | H |
| cyclohexyl | H | H | H | H, |
| and other like compounds. | | | | |

The catalysts in the instant cyclodehydration reaction are inorganic zinc salts which are soluble in the formamide reactant, carboxamide reactant or liquid reaction medium. The term "soluble" is not meant to imply that the zinc salts are soluble or miscible in all proportions with the formamide, carboxamide or liquid reaction medium but instead has at least a minimum solubility (e.g., about 100 parts per million or more) at reaction temperatures. The zinc salts are used in the process in merely small but catalytic amounts. Normally, the zinc salts are charged in amounts of from about 0.005 to about 0.4 mole of zinc salt per mole of formamide reactant but more or less of the zinc salts can be used, if desired. Zinc salts derived from strong inorganic mineral acids (sulfuric, nitric, hydrochloric, phosphoric, etc.) and other strong acids hypophosphorous acid, sulfonic acid, etc.) are preferred for this invention. The strength of the acids described is a measure of the concentration of the hydrogen ion that results from ionization in water. The approximate pH values of the preferred acids are in a range of from about 0.1 to about 2.4. Weaker inorganic acids such as hydrogen sulfide, arsenious acid, boric acid, etc. may be useful in the preparation of the zinc salts but are not as efficient (i.e., result in lower yields) as the stronger acids. Approximate pH values of the acids suitable for this invention are based on measurements made at 25° C. and reported in the *CRC Handbook of Chemistry and Physics*, 58th edition, CRC Press, 1977-1978, page D-135. Suitable such salts include, for example, zinc sulfate, bisulfate, chloride, bromide, iodide, and the like. Zinc chloride and zinc sulfate are the preferred catalysts.

The instant cyclodehydration reaction may be conducted neat or in solution with a suitable inert solvent. By "inert" is meant inert in the process. Suitable such inert solvents include, for example, chlorinated hydrocarbon solvents, aromatic hydrocarbons, cycloaliphatic hydrocarbons, and aliphatic hydrocarbons and the like. We prefer, however, to conduct the reaction neat (i.e., that is without any solvent added).

The reaction temperature must, obviously, be sufficient to promote the cyclodehydration reaction and is normally selected in the range of from about 140° C. to about 270° C. Preferred reaction rates have been observed at temperatures of from about 160° C. to about 220° C. The instant cyclodehydration reaction is also preferably conducted under reduced pressure. This facilitates product recovery in that frequently a reaction temperature may be chosen which is above the boiling point of the 2-H-2-oxazoline or 2-substituted-2-oxazoline product and below the boiling point of the N-(β-hydroxyalkyl)formamide or N-(β-hydroxyalkyl)carboxamide. In this manner, the 2-H-2-oxazoline or 2-substituted-2-oxazoline can be removed from the reaction mixture as a volatile gas essentially as it is formed. This is very desirable since the instant cyclodehydration reaction is a reversible process and by removing the product the reaction is forced to completion by substantially reducing the reverse reaction. Water normally codistills with the 2-H-2-oxazoline or 2-substituted-2-oxazoline product.

The instant process may be conducted in a batch process or by a continuous process. In the continuous process, of course, the N-(β-hydroxyalkyl)formamide or carboxamide reactant is metered into the reaction vessel at essentially the same rate as the oxazoline product and water are removed.

EXPERIMENTAL

The following examples will further illustrate the invention.

EXAMPLE 1

Preparation of 2-H-2-Oxazoline

Zinc chloride (5 g) and N-(β-hydroxyethyl)formamide (20–30 g) were charged to a reaction vessel equipped with a heating means, a stirring means, an addition funnel, a distillation head, condenser and receiver. The pressure over the reaction mixture was lowered to 50 mm Hg using a water aspirator and the mixture heated to a pot temperature of approximately 175° C. When the reaction began, as evidenced by the appearance of an overhead distillate, the dropwise addition of more formamide reactant was started. The formamide feed was stopped when the catalysts began to be deactivated, as evidenced by the formation of a very dark material in the bottom of the reaction vessel and a rapidly rising head temperature. The water-white overheads were continuously collected and when the reaction was complete, the overheads were extracted with chloroform to remove the 2-H-2-oxazoline from the water which codistilled. Distillation of the chloroform extracts at elevated temperature and atmospheric pressure using a 15-plate Oldershaw column gave the pure 2-H-2-oxazoline boiling at 98° C. The oxazoline product was produced in 70.9 percent yield in the process.

EXAMPLE 2

2-H-2-Oxazoline was produced in 75.6 percent yield, based on formamide charged, following the procedure described in Example 1 except using the amine/acid salt formed by blending equimolar amounts of formic acid with ethanolamine in place of the N-(β-hydroxyethyl)-formamide.

EXAMPLE 3

2-H-2-Oxazoline was produced in 56.1 percent yield, based on formamide charged, following the procedure described in Example 1 except using ZnSO$_4$.7H$_2$O as the catalyst.

Other 2-H-2-oxazolines can be similarly prepared using zinc chloride as the catalyst and other N-(β-hydroxyalkyl)formamides as the reactants or by using other combinations of catalysts and formamide reactants as set forth above.

EXAMPLE 4

Preparation of 2-Substituted-2-Oxazoline

Zinc oxide (10.0 g) and 95.4 percent pure N-(β-hydroxyethyl)propionamide (20.0 g) were charged to a reaction vessel equipped with a stirring means, a metering pump, and a 5-plate Oldershaw distillation column with a take-off head. The pressure over the reaction mixture was adjusted to 50 mm Hg and the reaction mixture heated to 200° C. The reaction mixture was held at 200° C. and 95.4 percent pure N-(β-hydroxyethyl)propionamide (290 g) was pumped in at approximately 0.9 g/min to the system. As the propionamide was added to the reaction mixture, a water-white distillate was collected overhead through the distillation apparatus at a head temperature of 40° C.–45° C. After the addition of the propionamide was complete, the pot was heated to 220° C. to drive off the last amounts of 2-ethyl-2-oxazoline. The overhead distillate temperature reached a maximum of 41° C. during this post-heating step. A total of 294.8 g of water-white distillate was thus obtained overhead leaving 21.7 g of a tan, wet paste remaining in the pot. Analysis of the distillate overheads by gas chromatography using an internal standard and also a Karl Fischer water titration showed the material to be 2-ethyl-2-oxazoline, water and very minor amounts of unreacted propionamide and 2-methyl-2-oxazoline. The impurities in the propionamide reactant were: water (approximately 1 percent); monoethanolamine (approximately 2–3 percent); and the amido-ester of propionic acid and monoethanolamine (approximately 1 percent).

The oxazoline was produced in 83.0 percent yield, based on the pure N-(β-hydroxyethyl)propionamide charged to the system. The amount of water produced according to analysis was 93.0 percent of theory. The 2-ethyl-2-oxazoline can be easily separated from the mixture by selective extraction using diethylbenzene followed by distillation.

EXAMPLES 5–8

Using substantially the same technique as described in Example 4, except that the catalyst was varied, the reactions summarized in Table A were conducted with the indicated results.

TABLE A

| Ex. | Catalyst | Percent Yield |
| --- | --- | --- |
| 5 | Zn(OH)$_2$ | 86.3 |
| 6 | ZnCl$_2$ | 94.5 |
| 7 | ZnI$_2$ | 91.5 |
| 8 | ZnSO$_4$.7H$_2$O | 91.9 |

What is claimed is:

1. A cyclodehydration process for making a 2-R-2-oxazoline wherein R is hydrogen, a hydrocarbyl or an inertly-substituted hydrocarbyl, which comprises the steps of reacting by contacting in liquid phase, an N-(2-hydroxyalkyl)carboxamide corresponding to the formula:

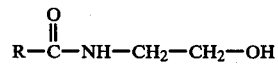

wherein R is as defined above, or a carboxylic acid/amine salt precursor of said N-(2-hydroxyethyl)carboxamide with a small but catalytic amount of an inorganic zinc salt of sulfuric, nitric, hydrochloric, hydrobromic, hydroiodic, phosphoric or hypophosphorous acid.

2. The process defined by claim 1 wherein R is hydrogen, methyl, ethyl, or phenyl.

3. The process defined by claim 2 wherein R is methyl or ethyl.

4. The process defined by claim 1 wherein said catalyst is charged in amounts of from about 0.005 to about 0.4 mole of inorganic zinc salt per mole of carboxamide reactant.

5. The process defined by claim 1 wherein said catalyst is zinc chloride or zinc sulfate.

6. The process defined by claim 1 wherein the process is conducted under conditions of temperature and pressure such that the 2-substituted-2-oxazoline product is removed from the reaction mixture as a volatile gas essentially as it is formed.

7. The process defined by claim 6 wherein said catalyst is zinc chloride, zinc sulfate or zinc iodide and wherein said carboxamide is N-(2-hydroxyethyl)-propionamide.

8. The process defined by claim 7 wherein said catalyst is charged in amounts of from about 0.005 to about 0.4 mole of inorganic zinc salt per mole of carboxamide reactant.

* * * * *

UNITED STATES PATENT AND TRADEMARK OFFICE
CERTIFICATE OF CORRECTION

PATENT NO. : 4,443,611
DATED : April 17, 1984
INVENTOR(S) : Mark E. Kaiser

It is certified that error appears in the above-identified patent and that said Letters Patent is hereby corrected as shown below:

Column 2, line 51, "$R_2$" should read --$R_3$--.

Column 3, Table II, line 4 of column $R_4$, insert --H--.

Column 3, line 48, "hypophosphorous" should read --(hypophosphorous--.

Signed and Sealed this

Fifteenth Day of July 1986

[SEAL]

Attest:

DONALD J. QUIGG

Attesting Officer

Commissioner of Patents and Trademarks